US012029473B2

(12) United States Patent
Whitlock et al.

(10) Patent No.: US 12,029,473 B2
(45) Date of Patent: Jul. 9, 2024

(54) SURGICAL INSTRUMENTS HAVING A JAW LOCKING MECHANISM

(71) Applicant: Intuitive Surgical Operations, Inc., Sunnyvale, CA (US)

(72) Inventors: Michael Steven Whitlock, Irvine, CA (US); William A. Burbank, Sandy Hook, CT (US); Scott Eugene Manzo, Shelton, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 851 days.

(21) Appl. No.: 16/427,427

(22) Filed: May 31, 2019

(65) Prior Publication Data

US 2019/0365458 A1   Dec. 5, 2019

Related U.S. Application Data

(60) Provisional application No. 62/678,405, filed on May 31, 2018.

(51) Int. Cl.
*A61B 18/14* (2006.01)
*A61B 17/29* (2006.01)
*A61B 18/00* (2006.01)
*A61B 34/30* (2016.01)

(52) U.S. Cl.
CPC .. *A61B 18/1447* (2013.01); *A61B 2017/2936* (2013.01); *A61B 2017/2946* (2013.01); *A61B 2018/0063* (2013.01); *A61B 2018/1455* (2013.01); *A61B 2034/302* (2016.02)

(58) Field of Classification Search
CPC ........ A61B 18/1447; A61B 2017/2936; A61B 2017/2946; A61B 2018/0063; A61B 2018/1455; A61B 2034/302; A61B 34/30; A61B 2017/2943; A61B 2018/00607
See application file for complete search history.

(56) References Cited

U.S. PATENT DOCUMENTS

| | | | |
|---|---|---|---|
| 4,305,539 | A | 12/1981 | Korolkov et al. |
| 4,319,576 | A | 3/1982 | Rothfuss |
| 4,407,286 | A | 10/1983 | Noiles et al. |

(Continued)

FOREIGN PATENT DOCUMENTS

| | | |
|---|---|---|
| CN | 112165909 A | 1/2021 |
| EP | 0277532 B1 | 8/1990 |

(Continued)

OTHER PUBLICATIONS

International Search Report and Written Opinion for Application No. PCT/US2020/054568, mailed Jan. 29, 2021, 13 pages.

(Continued)

*Primary Examiner* — Ronald Hupczey, Jr.
(74) *Attorney, Agent, or Firm* — FARBER LLC

(57) ABSTRACT

A surgical instrument having a jaw lock includes first jaw and second jaws that are moveable from an open position to a closed position. At least one of the jaws includes a jaw slot having a jaw closing portion and a jaw locking portion. A pin positioned within the jaw slot is advanced by a blade. The blade includes a cutting edge and a notch defining a first edge configured to advance the pin to move the jaws to, and secure the jaws in, the closed position.

13 Claims, 13 Drawing Sheets

(56) References Cited

U.S. PATENT DOCUMENTS

| | | | |
|---|---|---|---|
| 4,429,695 A * | 2/1984 | Green | A61B 17/07207 227/176.1 |
| 4,509,518 A * | 4/1985 | McGarry | A61B 17/128 606/143 |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,874 A | 1/1987 | Chow et al. | |
| 4,767,044 A | 8/1988 | Green | |
| 4,809,695 A | 3/1989 | Gwathmey et al. | |
| 4,848,637 A | 7/1989 | Pruitt | |
| 4,892,244 A | 1/1990 | Fox et al. | |
| 4,930,503 A | 6/1990 | Pruitt | |
| 4,978,049 A | 12/1990 | Green | |
| 5,027,834 A | 7/1991 | Pruitt | |
| 5,040,715 A | 8/1991 | Green et al. | |
| 5,133,735 A * | 7/1992 | Slater | A61B 18/1445 606/174 |
| 5,133,736 A * | 7/1992 | Bales, Jr. | A61B 10/06 606/174 |
| 5,147,357 A * | 9/1992 | Rose | A61B 17/29 606/49 |
| 5,180,092 A | 1/1993 | Crainich | |
| 5,275,323 A | 1/1994 | Schulze et al. | |
| 5,307,976 A | 5/1994 | Olson et al. | |
| 5,312,023 A | 5/1994 | Green et al. | |
| 5,334,183 A | 8/1994 | Wuchinich | |
| 5,342,395 A | 8/1994 | Jarrett et al. | |
| 5,342,396 A | 8/1994 | Cook | |
| 5,366,133 A | 11/1994 | Geiste | |
| 5,452,836 A | 9/1995 | Huitema et al. | |
| 5,452,837 A | 9/1995 | Williamson, IV et al. | |
| 5,465,895 A | 11/1995 | Knodel et al. | |
| 5,480,089 A | 1/1996 | Blewett | |
| 5,484,095 A | 1/1996 | Green et al. | |
| 5,484,451 A | 1/1996 | Akopov et al. | |
| 5,487,500 A | 1/1996 | Knodel et al. | |
| 5,497,931 A | 3/1996 | Nakamura | |
| 5,533,521 A | 7/1996 | Granger | |
| 5,540,375 A | 7/1996 | Bolanos et al. | |
| 5,554,164 A | 9/1996 | Wilson et al. | |
| 5,560,530 A | 10/1996 | Bolanos et al. | |
| 5,562,239 A | 10/1996 | Boiarski et al. | |
| 5,564,615 A | 10/1996 | Bishop et al. | |
| 5,571,116 A | 11/1996 | Bolanos et al. | |
| 5,571,285 A | 11/1996 | Chow et al. | |
| 5,573,534 A | 11/1996 | Stone | |
| 5,615,820 A | 4/1997 | Viola | |
| 5,624,452 A | 4/1997 | Yates | |
| 5,628,446 A | 5/1997 | Geiste et al. | |
| 5,651,491 A | 7/1997 | Heaton et al. | |
| 5,652,849 A | 7/1997 | Conway et al. | |
| 5,667,526 A | 9/1997 | Cayford et al. | |
| 5,673,840 A | 10/1997 | Schulze et al. | |
| 5,673,842 A | 10/1997 | Bittner et al. | |
| 5,676,674 A | 10/1997 | Bolanos et al. | |
| 5,688,269 A | 11/1997 | Newton et al. | |
| 5,690,269 A | 11/1997 | Bolanos et al. | |
| 5,693,042 A | 12/1997 | Boiarski et al. | |
| 5,697,542 A | 12/1997 | Knodel et al. | |
| 5,700,270 A | 12/1997 | Peyser et al. | |
| 5,700,276 A | 12/1997 | Benecke | |
| 5,709,680 A | 1/1998 | Yates et al. | |
| 5,752,644 A | 5/1998 | Bolanos et al. | |
| 5,752,973 A | 5/1998 | Kieturakis et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,792,135 A | 8/1998 | Madhani et al. | |
| 5,820,009 A | 10/1998 | Melling et al. | |
| 5,826,776 A | 10/1998 | Schulze et al. | |
| 5,833,695 A | 11/1998 | Yoon | |
| 5,865,361 A | 2/1999 | Milliman et al. | |
| 5,871,135 A | 2/1999 | Williamson, IV et al. | |
| 5,911,353 A | 6/1999 | Bolanos et al. | |
| 5,915,616 A | 6/1999 | Viola et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 5,959,892 A | 9/1999 | Lin et al. | |
| 6,032,849 A | 3/2000 | Mastri et al. | |
| 6,050,996 A | 4/2000 | Schmaltz et al. | |
| 6,079,606 A | 6/2000 | Milliman et al. | |
| 6,174,309 B1 | 1/2001 | Wrublewski et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,330,956 B1 | 12/2001 | Willinger | |
| 6,330,965 B1 | 12/2001 | Milliman et al. | |
| 6,488,196 B1 | 12/2002 | Fenton, Jr. | |
| 6,503,259 B2 | 1/2003 | Huxel et al. | |
| 6,585,735 B1 * | 7/2003 | Frazier | A61B 18/1445 606/208 |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,786,382 B1 | 9/2004 | Hoffman | |
| 6,817,974 B2 | 11/2004 | Cooper et al. | |
| 6,877,647 B2 | 4/2005 | Green et al. | |
| 6,905,057 B2 | 6/2005 | Swayze et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,986,451 B1 | 1/2006 | Mastri et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,114,642 B2 | 10/2006 | Whitman | |
| 7,128,253 B2 | 10/2006 | Mastri et al. | |
| 7,140,527 B2 | 11/2006 | Ehrenfels et al. | |
| 7,140,528 B2 | 11/2006 | Shelton, IV et al. | |
| 7,258,262 B2 | 8/2007 | Mastri et al. | |
| 7,308,998 B2 | 12/2007 | Mastri et al. | |
| 7,328,828 B2 | 2/2008 | Ortiz et al. | |
| 7,380,695 B2 | 6/2008 | Doll et al. | |
| 7,380,696 B2 | 6/2008 | Shelton, IV et al. | |
| 7,398,908 B2 | 7/2008 | Holsten et al. | |
| 7,401,721 B2 | 7/2008 | Holsten et al. | |
| 7,407,075 B2 | 8/2008 | Holsten et al. | |
| 7,455,676 B2 | 11/2008 | Holsten et al. | |
| 7,472,814 B2 | 1/2009 | Mastri et al. | |
| 7,481,349 B2 | 1/2009 | Holsten et al. | |
| 7,494,039 B2 | 2/2009 | Racenet et al. | |
| 7,565,993 B2 | 7/2009 | Milliman et al. | |
| 7,588,174 B2 | 9/2009 | Holsten et al. | |
| 7,654,431 B2 | 2/2010 | Hueil et al. | |
| 7,658,312 B2 | 2/2010 | Vidal et al. | |
| 7,673,783 B2 | 3/2010 | Morgan et al. | |
| 7,699,835 B2 | 4/2010 | Lee et al. | |
| 7,721,930 B2 | 5/2010 | McKenna et al. | |
| 7,726,539 B2 | 6/2010 | Holsten et al. | |
| 7,770,774 B2 | 8/2010 | Mastri et al. | |
| 7,794,475 B2 | 9/2010 | Hess et al. | |
| 7,832,611 B2 | 11/2010 | Boyden et al. | |
| 7,837,079 B2 | 11/2010 | Holsten et al. | |
| 7,866,526 B2 | 1/2011 | Green et al. | |
| 7,942,303 B2 | 5/2011 | Shah et al. | |
| 7,950,561 B2 | 5/2011 | Aranyi | |
| 8,070,035 B2 | 12/2011 | Holsten et al. | |
| 8,083,118 B2 | 12/2011 | Milliman et al. | |
| 8,127,975 B2 | 3/2012 | Olson et al. | |
| 8,157,152 B2 | 4/2012 | Holsten et al. | |
| 8,272,553 B2 | 9/2012 | Mastri et al. | |
| 8,308,042 B2 | 11/2012 | Aranyi | |
| 8,348,127 B2 | 1/2013 | Marczyk | |

(56) References Cited

U.S. PATENT DOCUMENTS

| | | |
|---|---|---|
| 8,365,972 B2 | 2/2013 | Aranyi et al. |
| 8,371,492 B2 | 2/2013 | Aranyi et al. |
| 8,439,246 B1 | 5/2013 | Knodel |
| 8,490,851 B2 | 7/2013 | Blier et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,701,960 B1 | 4/2014 | Manoux et al. |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 11,723,661 B2 | 8/2023 | Wixey et al. |
| 2002/0165562 A1 | 11/2002 | Grant et al. |
| 2003/0135204 A1 | 7/2003 | Lee et al. |
| 2003/0181910 A1* | 9/2003 | Dycus ............... A61B 18/1445 606/51 |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1* | 5/2005 | Ahlberg ............... A61B 17/282 606/205 |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0161190 A1* | 7/2006 | Gadberry ........... A61B 18/1445 606/174 |
| 2006/0190031 A1 | 8/2006 | Wales et al. |
| 2006/0217706 A1 | 9/2006 | Lau et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2008/0086114 A1 | 4/2008 | Schmitz et al. |
| 2008/0308607 A1 | 12/2008 | Timm et al. |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli et al. |
| 2010/0145334 A1* | 6/2010 | Olson ............... A61B 18/1445 606/51 |
| 2010/0179545 A1* | 7/2010 | Twomey ............ A61B 18/1445 606/51 |
| 2010/0198248 A1 | 8/2010 | Vakharia |
| 2010/0331857 A1 | 12/2010 | Doyle et al. |
| 2011/0022078 A1 | 1/2011 | Hinman |
| 2011/0036891 A1 | 2/2011 | Zemlok et al. |
| 2011/0118707 A1 | 5/2011 | Burbank |
| 2011/0121050 A1 | 5/2011 | Nicholas et al. |
| 2011/0152879 A1 | 6/2011 | Williams |
| 2011/0174863 A1 | 7/2011 | Shelton, IV et al. |
| 2011/0251612 A1* | 10/2011 | Faller ............... A61B 18/1445 606/52 |
| 2011/0251613 A1* | 10/2011 | Guerra ............... A61B 17/295 606/52 |
| 2011/0288573 A1 | 11/2011 | Yates et al. |
| 2011/0290851 A1 | 12/2011 | Shelton, IV |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2012/0289999 A1* | 11/2012 | Frank ............... A61B 17/062 606/205 |
| 2012/0298719 A1 | 11/2012 | Shelton, IV et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1* | 11/2013 | Allen, IV ........... A61B 18/1445 606/205 |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0021239 A1 | 1/2014 | Kostrzewski |
| 2014/0025071 A1* | 1/2014 | Sims ............... A61B 17/2812 606/46 |
| 2014/0100600 A1 | 4/2014 | Kendrick |
| 2014/0175152 A1 | 6/2014 | Hess et al. |
| 2014/0180286 A1* | 6/2014 | Marczyk ........... A61B 17/2909 606/49 |
| 2014/0183244 A1 | 7/2014 | Duque et al. |
| 2014/0200596 A1 | 7/2014 | Weir et al. |
| 2014/0214049 A1 | 7/2014 | Jeong et al. |
| 2014/0257331 A1 | 9/2014 | Kim et al. |
| 2014/0263546 A1 | 9/2014 | Aranyi |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1* | 11/2014 | Faller ............... A61B 18/1445 606/52 |
| 2014/0343569 A1 | 11/2014 | Turner |

(56) References Cited

U.S. PATENT DOCUMENTS

| | | |
|---|---|---|
| 2014/0364851 A1* | 12/2014 | Batross .............. A61B 18/1445 606/45 |
| 2015/0173789 A1 | 6/2015 | Baxter, III et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297235 A1 | 10/2015 | Harris et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0089148 A1 | 3/2016 | Harris et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0338764 A1* | 11/2016 | Krastins ................ A61B 17/29 |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1* | 5/2017 | Tetzlaff .............. A61B 18/1442 |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310948 A1* | 11/2018 | Stamm .............. A61B 18/1445 |
| 2018/0317915 A1 | 11/2018 | McDonald, II |
| 2019/0000454 A1 | 1/2019 | Swayze et al. |
| 2019/0015124 A1* | 1/2019 | Williams .............. A61B 17/282 |
| 2019/0059894 A1 | 2/2019 | Kumada et al. |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0133571 A1 | 5/2019 | Racenet et al. |
| 2019/0142531 A1 | 5/2019 | Wentworth et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0290374 A1 | 9/2019 | Ramadorai |
| 2019/0298356 A1 | 10/2019 | Shelton, IV et al. |
| 2019/0314107 A1 | 10/2019 | Worrell et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1 | 9/2021 | Fanelli et al. |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1* | 1/2022 | Wilson ................ A61B 18/1445 |
| 2022/0054130 A1* | 2/2022 | Overmyer ........ A61B 17/07207 |
| 2022/0061836 A1* | 3/2022 | Parihar .............. A61B 17/1155 |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1* | 3/2022 | Egan .................. A61B 17/0469 |
| 2022/0125428 A1 | 4/2022 | Ragosta et al. |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |
| 2023/0225731 A1 | 7/2023 | Burbank |

FOREIGN PATENT DOCUMENTS

| | | |
|---|---|---|
| EP | 0277529 B1 | 4/1993 |
| EP | 0641546 A1 | 3/1995 |
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 2777530 A1 | 9/2014 |
| EP | 2777532 A2 | 9/2014 |
| EP | 3000408 A2 | 3/2016 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |
| WO | WO-2020081960 A1 | 4/2020 |
| WO | WO-2020131692 A1 | 6/2020 |

OTHER PUBLICATIONS

International Preliminary Report on Patentability for Application No. PCT/US2019/017646, mailed on Aug. 27, 2020, 10 pages.

International Preliminary Report on Patentability for Application No. PCT/US2019/019501, mailed Sep. 3, 2020, 7 pages.

International Search Report and Written Opinion for Application No. PCT/US2020/025655, mailed Jul. 22, 2020, 8 pages.

(56) References Cited

OTHER PUBLICATIONS

International Search Report and Written Opinion for Application No. PCT/US19/17646, mailed on Apr. 16, 2019, 11 pages.
International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US2020/020672, mailed Jun. 29, 2020, 10 pages.
International Search Report and Written Opinion for Application No. PCT/US2020/033481, mailed Sep. 3, 2020, 22 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Search Report and Written Opinion for Application No. PCT/US2021/012284, mailed May 6, 2021, 23 pages.
European Search Report (Corrected version) for Application No. EP19750317.0, mailed on Mar. 28, 2022, 26 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
International Search Report and Written Opinion for Application No. PCT/US202 1/065544 mailed Jun. 2, 2022, 21 pages.
International Search Report and Written Opinion for Application No. PCT/US2021/065308, mailed Apr. 21, 2022. 13 pages.

* cited by examiner

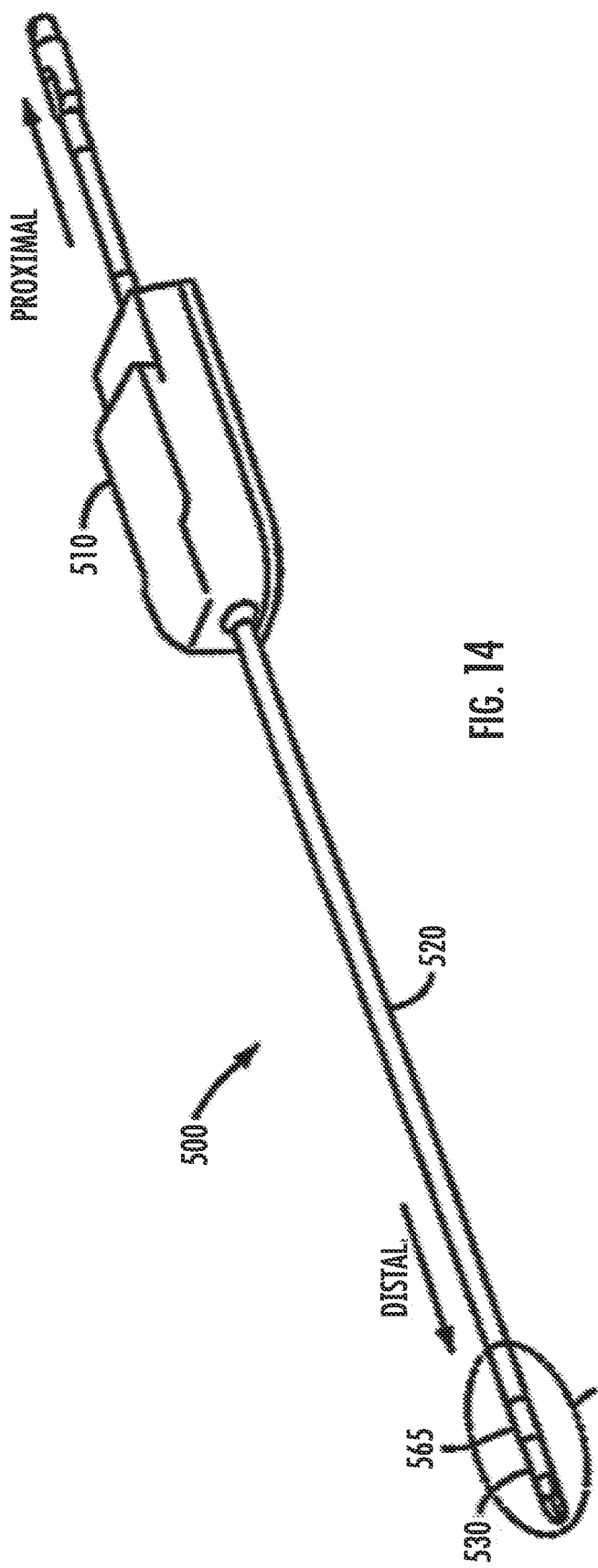

SURGICAL INSTRUMENTS HAVING A JAW LOCKING MECHANISM

BACKGROUND

Energy may be used to fuse tissue during certain surgical procedures. When using energy to fuse tissue, two or more tissues (e.g., a tissue bundle) are typically gripped between two electrodes, and electrosurgical energy is passed between the electrodes in order to fuse the tissues together. An example of such tissues includes the opposing walls of a blood vessel. In this way, the blood vessel can be fused closed, resulting in a sealing of the vessel at the fused region. Surgical instruments that perform this action are often referred to as sealing instruments (e.g., a "vessel sealer"). Such surgical instruments also can be used, for example, for cold cutting, tissue dissection, coagulation of tissue bundles generally (e.g., other than for sealing), and tissue manipulation/retraction. Once tissues, such as, for example, of a blood vessel, are fused together, the fused region can be safely cut without any resulting bleeding.

For both convenience and cutting accuracy, surgical instruments have been developed that utilize an end effector that integrates the use of tissue fusing and cutting. Instruments for minimally invasive surgery (e.g., laparoscopic, thoracoscopic, etc.) typically have a surgical end effector mounted at the distal end of a long shaft that is inserted through an opening (e.g., body wall incision, natural orifice) to reach a surgical site. In some cases, an articulating wrist mechanism may be mounted at the instrument's distal end to support the end effector and change its orientation with reference to the shaft's longitudinal axis.

Surgical instruments often include drive members configured to translate various components distally upon actuation of the surgical instrument. For example, many surgical instruments currently utilize I-beams, E-beams, or other similar drive members. I-beams and other similar structures require a certain instrument width along the length of the instrument to maintain structural integrity. Additionally, I-beams typically require horizontally oriented tracks or channels formed within the instrument jaws to permit distal travel through the jaws, complicating both manufacturing and achieving electrical isolation of various components.

It can be appreciated that minimizing the outer diameter of the shaft, wrist, and end effector may be desirable to reduce patient trauma during minimally invasive surgery. It is also advantageous to minimize the size of the surgical instrument, and the number of components contained therein to simplify manufacturing, while still preserving function. It may also be desirable to have a mechanism for keeping the jaws locked in a closed position during sealing and cutting.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical instruments having a first jaw and a second jaw. The first and second jaws are moveable from an open position, to a closed position. At least one of the jaws includes a jaw slot having a jaw closing portion and a jaw locking portion. A pin positioned within the jaw slot is advanced by a blade including a cutting edge and a notch defining a first edge configured to engage and advance the pin to move the jaws to, and secure the jaws in, the closed position.

In one aspect, a surgical instrument in accordance with this disclosure includes an elongated shaft. An end effector is mounted on the distal portion of the elongated shaft, and includes a first jaw and a second jaw. The first jaw and the second jaw are movable between an open position to receive tissue, and a closed position to grasp tissue between the jaws. The first jaw includes a jaw slot having a proximal jaw closing portion, and a distal jaw locking portion. The surgical instrument further includes a pin positioned within the jaw slot, and a blade. The blade has a cutting edge and a notch, the notch defining a first edge configured to engage and distally advance the pin through the first jaw closing portion of the jaw slot to pivot the jaws to the closed position. Upon further distal movement of the blade, the pin is advanced through the jaw locking portion of the jaw slot to secure the pin into a locked position.

BRIEF DESCRIPTION OF THE DRAWINGS

The above and other aspects, features, and advantages of the present surgical instruments having a jaw locking mechanism will become more apparent in light of the following detailed description when taken in conjunction with the accompanying drawings in which:

FIG. 14 is a perspective view of a teleoperated surgical instrument usable with an exemplary embodiment of the present teachings.

DETAILED DESCRIPTION

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in unnecessary detail.

The present disclosure relates to surgical instruments that include an upper jaw and lower jaw, where at least one of the jaws includes a cam slot that receives a pin. A blade may be driven distally to advance the pin from a proximal first position at which the jaws are in an open position, to a second distal position at which the jaws are locked in a closed position. While the following disclosure is presented with respect to surgical sealing devices, it should be understood that the present surgical instruments may be readily adapted for use in any type of surgical instrument that includes two jaws, such as clamping and cutting instruments, whether or not the surgical clamping and cutting instrument applies energy to seal tissue. The surgical instrument may be a minimally invasive (e.g., laparoscopic) instrument or an instrument used for open surgery.

Figure 1:
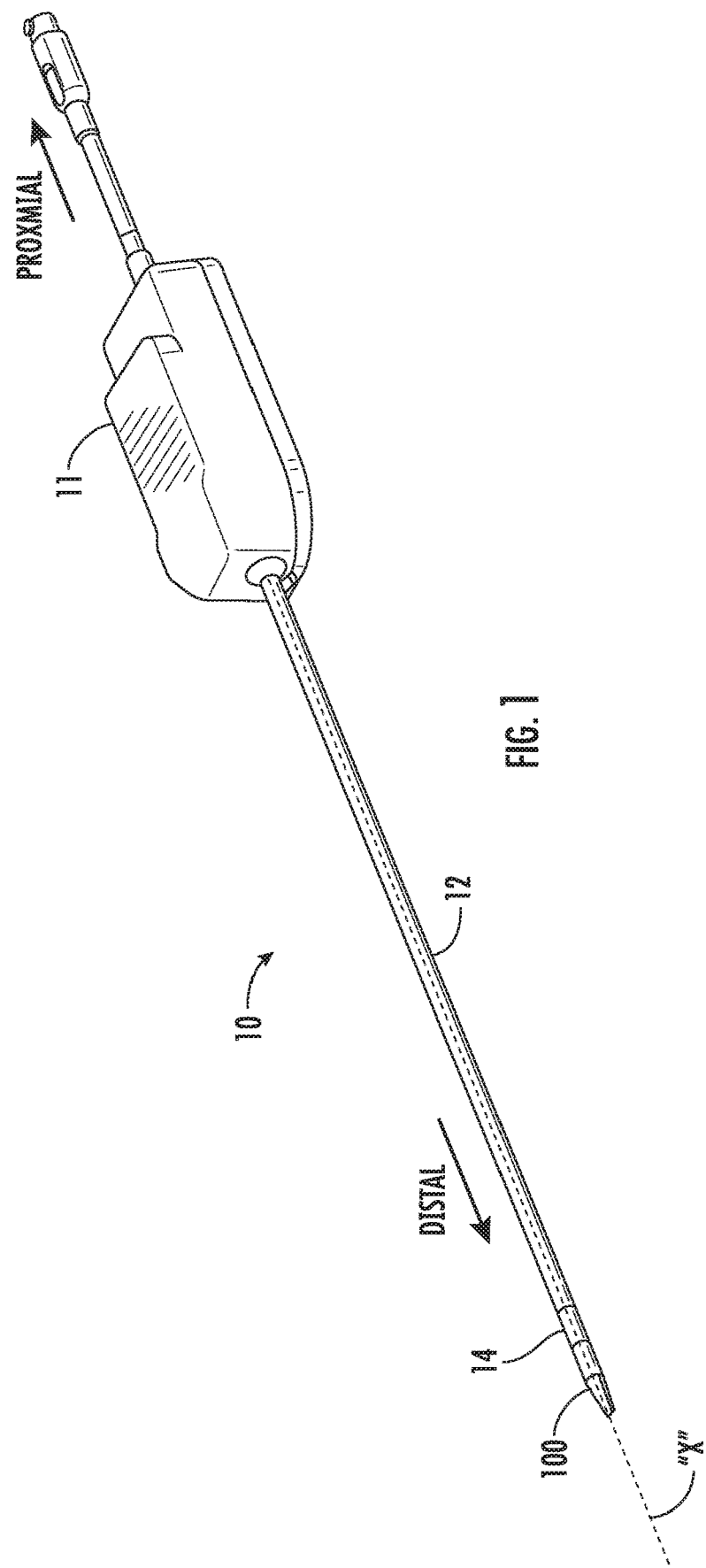
FIG. 1 is a diagrammatic perspective of a minimally invasive surgical instrument in accordance with an exemplary embodiment of the present disclosure.

FIG. 1 shows a diagrammatic perspective view of a minimally invasive surgical instrument 10, and various components thereof in accordance with an exemplary embodiment of the present disclosure. The directions "proximal" and "distal" are used herein to define the directions as shown in FIG. 1, with distal generally being in a direction closest to the surgical work site in the intended operational use of the instrument 10, for example, in use for performing surgical procedures. As shown in FIG. 1, instrument 10 generally includes a force/torque drive transmission mechanism 11, and an instrument shaft 12 mounted to the transmission mechanism 11. Shaft 12 defines a longitudinal axis "X". An integrated gripping, fusing, and cutting end effector 100 is disposed at the distal end of instrument 10, and an articulation wrist 14 is disposed between distal end of shaft 12 and end effector 100. Articulation wrist 14 includes a clevis 120, as described in more detail below.

In an exemplary embodiment, the instrument 10 is configured to be mounted on, and used with a minimally invasive surgical robotic system, such as those shown in U.S. Publication No. US 2015/0250530 A1 and U.S. Pat. No. 9,522,003, the entire disclosures of which are incorporated herein by reference. However, it is to be understood that the instrument may be a manual instrument or a electromechanically powered instrument. Exemplary manual and electromechanically powered instruments are shown, for example, in U.S. Pat. Nos. 8,696,665 and 9,161,803, respectively, the entire disclosures of which are incorporated herein by reference.

Figure 2:
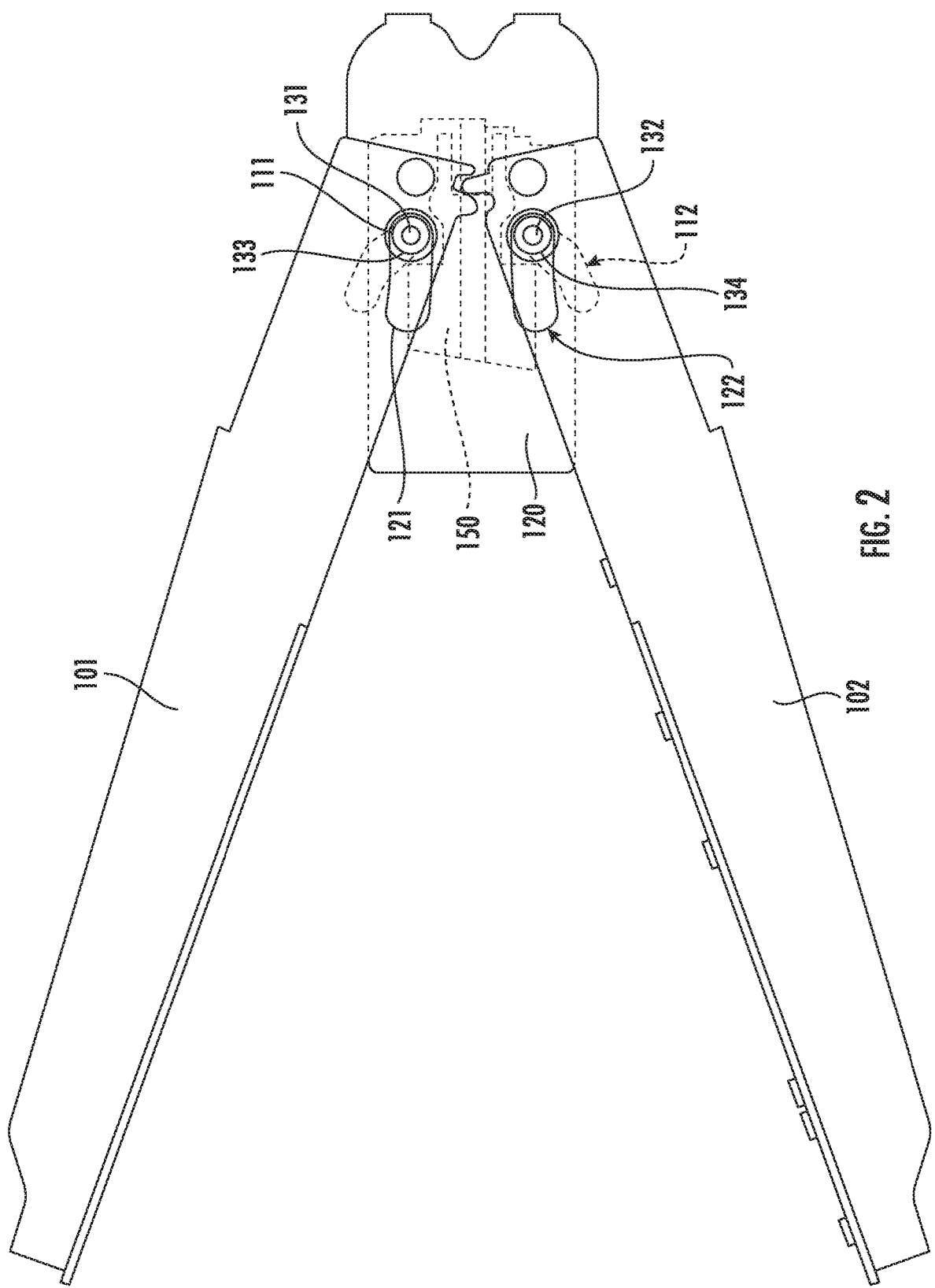
FIG. 2 depicts a partial cross-sectional side view of the distal end of a surgical instrument including an end effector and a clevis of an articulation wrist that provide a jaw lock in accordance with an embodiment of the present disclosure having the jaws in an open position.

As seen in FIG. 2, end effector 100 includes upper jaw 101 having a slot 111; lower jaw 102 having a slot 112; pins 131, 132 positioned within sleeves 133, 134; and blade 150. End effector 100 is mounted to clevis 120 (only one side shown in FIG. 2) of articulation wrist 14.

FIG. 2 shows upper and lower jaws 101, 102 in an open configuration, with pins 131, 132 in the proximal-most position of jaw slots 111 and 112, respectively. Blade 150 is similarly in a fully retracted, proximal position, and has not yet been actuated. Blade 150 is generally aligned with and driven along a central channel 105 (see FIG. 6) in one or both of jaws 101, 102.

Figure 3A:
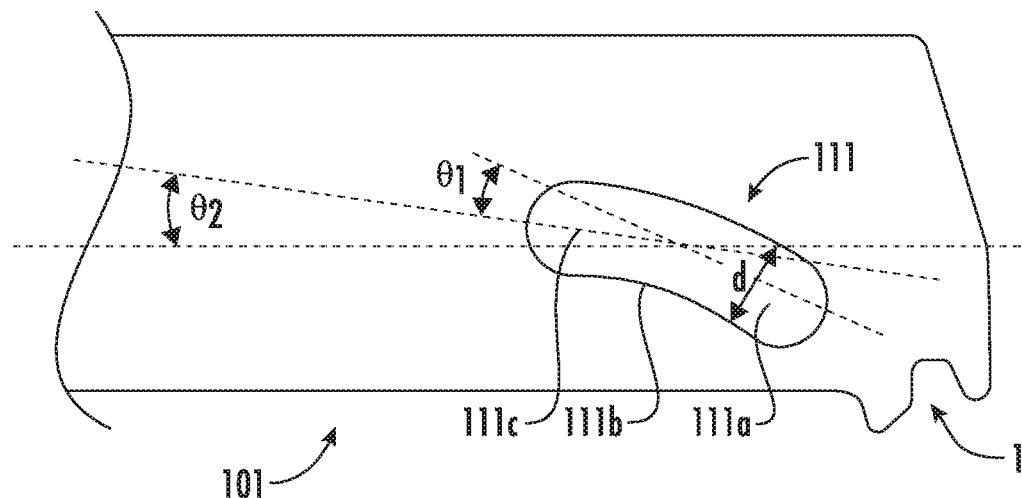
FIG. 3A shows a schematic view of the proximal end portion of an upper jaw of the embodiment of FIG. 2.
Figure 3B:
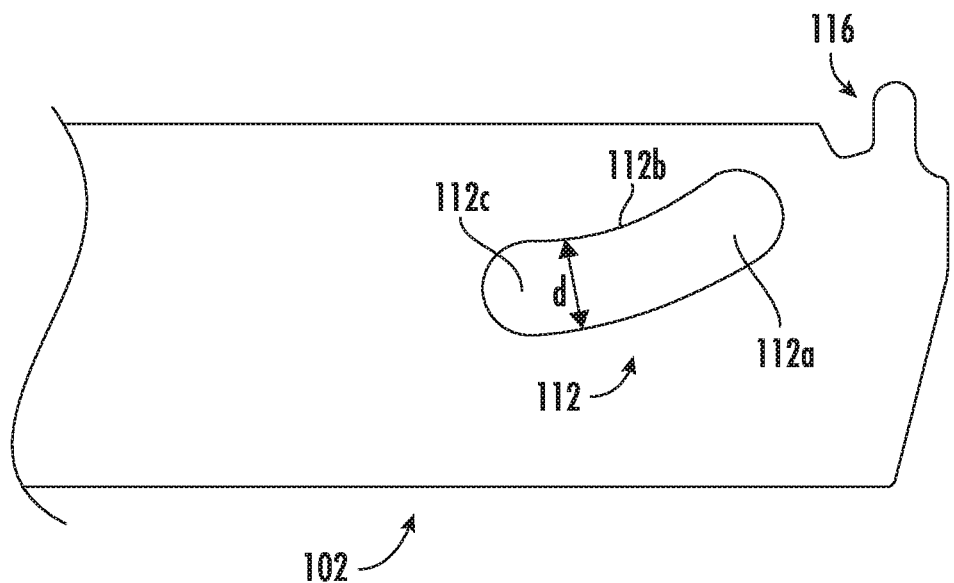
FIG. 3B shows a schematic view of the proximal end portion of a lower jaw of the embodiment of FIG. 2.

FIG. 3A depicts the proximal portion of upper jaw 101 including jaw slot 111 having proximal jaw-closing portion 111a, central portion 111b, and distal jaw-locking portion 111c. In embodiments, distal portion 111c may extend at an angle ($\varnothing_1$) from about 5 to about 30 degrees from proximal portion 111a of slot 111, in embodiments from about 10 to about 20 degrees. When the jaws are in the closed position, distal portion 111c may extend at an angle ($\varnothing_2$) from about 5 to about 30 degrees from longitudinal axis "X", in embodiments from about 10 to about 20 degrees. Distal jaw locking portion 11c includes edges 121d, 122d against which pins 131, 132 are wedged to lock jaws 101, 102 in a closed position (see FIG. 4). The width 'd' of jaw slot 111 is substantially similar to the diameter of pin 131. FIG. 3B depicts the proximal end portion of lower jaw 102 having a similar configuration to upper jaw 101. Jaws 101, 102 also include gear teeth 115, 116 respectively, to assist in maintaining jaw alignment during jaw movement.

In operation, upper jaw 101 may start in an open configuration, as pin 131 of upper jaw 101 rests in proximal jaw-closing portion 111a of jaw slot 111. As blade 150 is activated and translates distally, pin 131 moves distally along proximal jaw-closing portion 111a and jaw 101 begins to pivot towards a closed configuration. When pin 131 reaches central portion 111b, upper jaw 101 has pivoted to the closed configuration, but is not locked. Pin 131 is then further advanced distally into distal end 111c of jaw slot 111, where it is held by a friction fit, locking upper jaw 101 in the closed configuration. The lower jaw 102 as illustrated in FIG. 3B operates in substantially the same way as upper jaw 101 of FIG. 3A.

Figure 4:
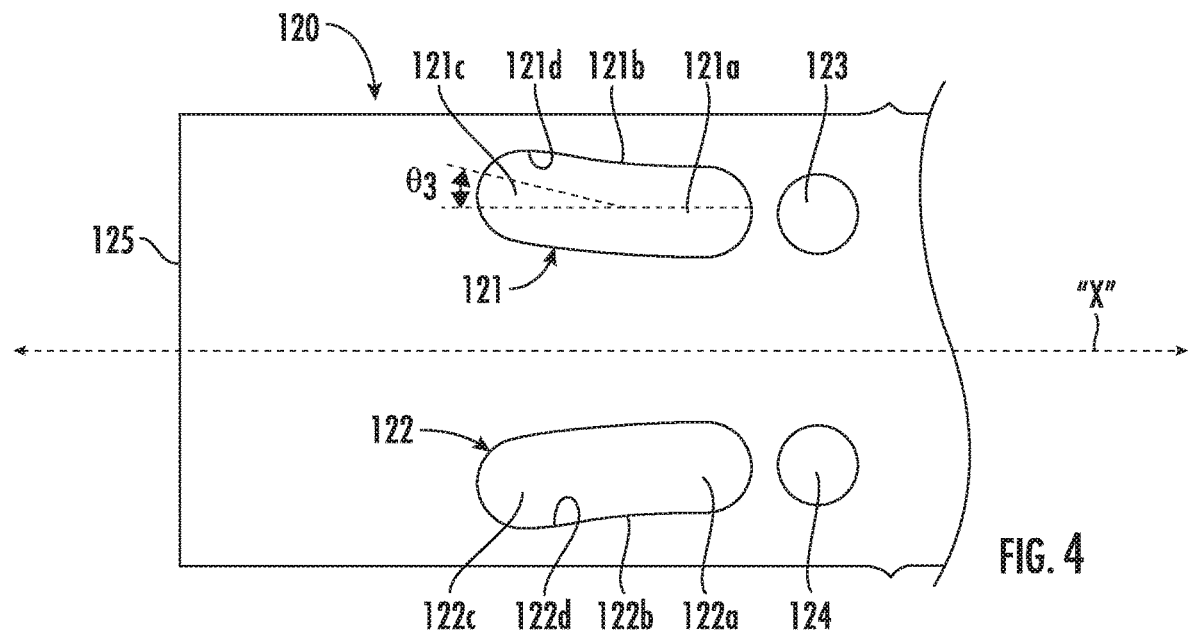
FIG. 4 is a schematic view of the distal end portion of the clevis of the embodiment of FIG. 2.
Figure 6:
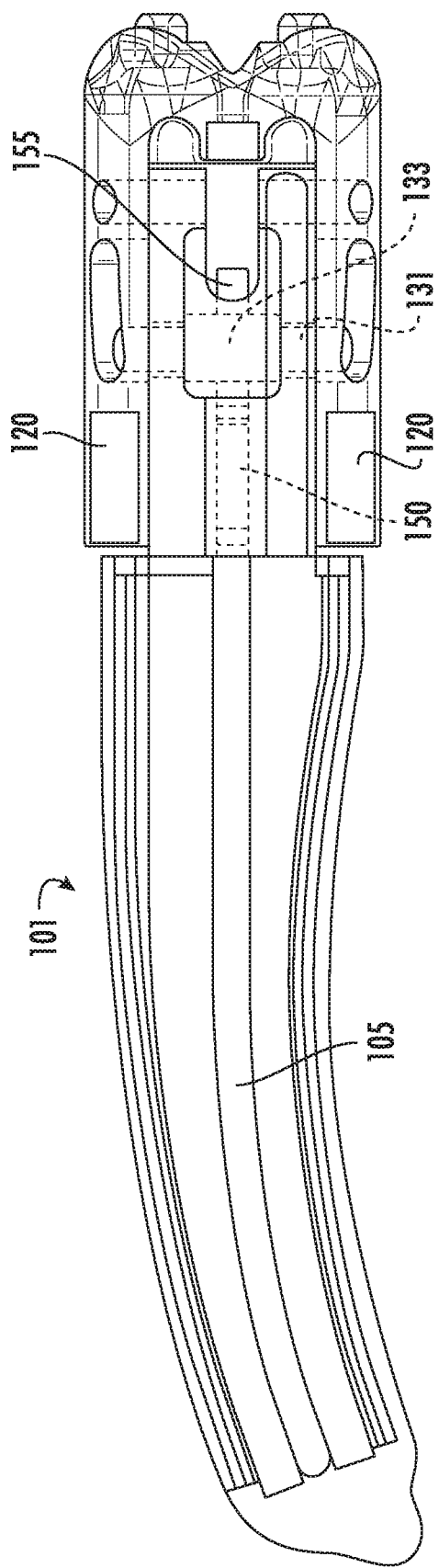
FIG. 6 is a bottom cross-sectional view of the surgical instrument of FIG. 2 showing the jaw lock mechanism activated.

FIG. 4 shows the distal end portion of clevis 120 having an upper clevis slot 121, a lower clevis slot 122, and a distal-most edge 125. As those skilled in the art will appreciate, (and as seen in FIG. 6) clevis 120 extends on both sides of jaws 101, 102, with each side of clevis 120 including the structures schematically shown in FIG. 4.

Upper clevis slot 121 may include proximal portion 121a, central portion 121b, distal portion 121c, and upper edge 121d. Proximal portion 121a of slot 121 is substantially parallel with longitudinal axis "X" of shaft 12 of surgical instrument 10. In embodiments, distal portion 121c extends at an angle ($\varnothing_3$) from about 5 to about 30 degrees from longitudinal axis "X", in embodiments from about 10 to about 20 degrees. Distal jaw locking portions 121c, 122c include edges 121d, 122d against which pins 131, 132 are wedged to lock jaws 101, 102 in a closed position. Openings 123, 124 are provided to receive pivot pins (not shown) to secure jaws 101, 102 to clevis 120. Slot 121 may be wider than the diameter of pins 131, 132 but less than the diameter of sleeves 133, 134. Lower clevis slot 122 may have a structure that is substantially similar to upper clevis slot 121.

Figure 5:
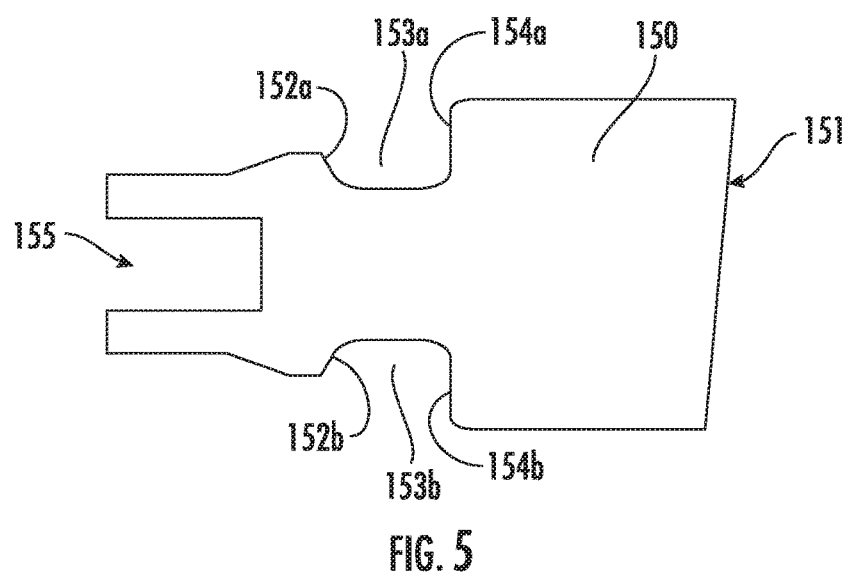
FIG. 5 shows a schematic view of the blade of the embodiment of FIG. 2.

FIG. 5 shows an illustrative blade 150 of the embodiment of FIG. 2. Blade 150 may include cutting edge 151 and notches 153a, 153b defining first edges 152a, 152b and second edges 154a, 154b. In the fully retracted, proximal position shown in FIG. 2, notches 153a, 153b of blade 150 are aligned with and receive sleeves 133, 134 respectively, so that upon distal translation of blade 150, first edges 152a,b of blade 150 may contact sleeves 133, 134 respectively, and translate pins 131, 132 in a distal direction. Sleeves 133, 134 are configured to ensure alignment of pins 131, 132 and prevent unwanted lateral motion as pins 131, 132 translate distally. Blade 150 also includes a drive engagement structure 155 at a distal portion thereof. Drive engagement structure 155 may be substantially U-shaped.

Drive engagement portion 155 is connected to a drive mechanism (not shown) that advances blade 150 distally and retracts blade 150 proximally. For example, blade 150 may be driven by a spring mechanism coupled to a series of drive cables, or by any other comparable driving mechanism that may be known by a person of ordinary skill in the art. Such drive mechanisms using articulating wrists are shown for example in U.S. Publication. No. 2015/0250530 the disclosure of which is hereby incorporated by reference in its entirety. As blade 150 travels distally, it translates through blade channel 105 (as best seen in FIG. 6) to cut tissue.

Figure 7:
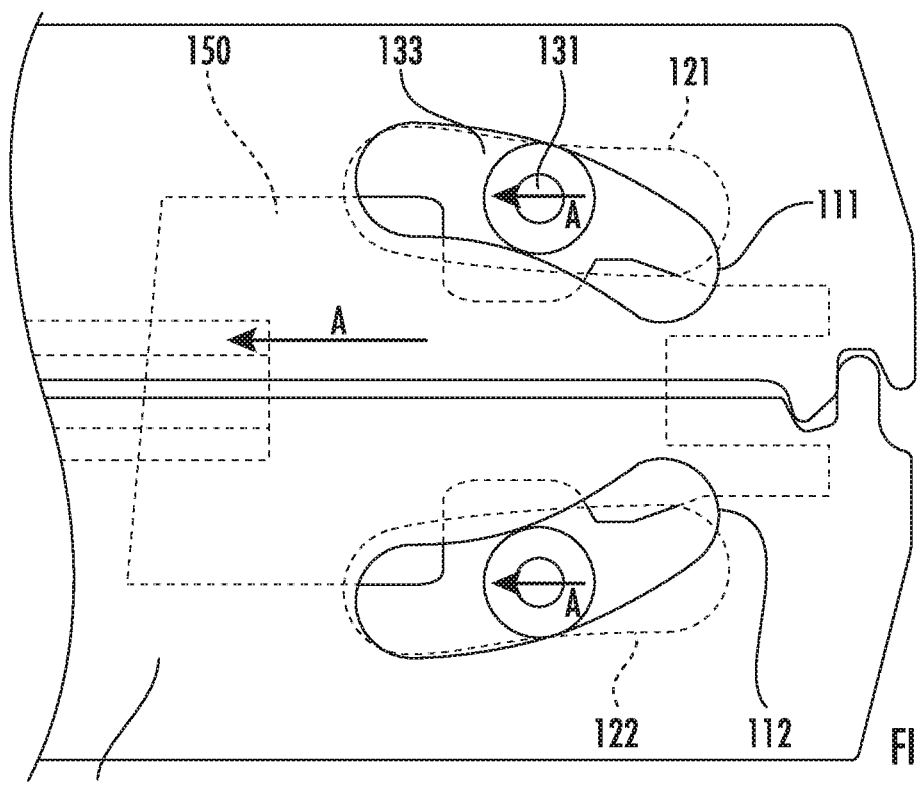
FIG. 7 is a partial cross-sectional side view of the surgical instrument in accordance with the embodiment of FIG. 2 illustrating the jaws in a closed, but unlocked, configuration.
Figure 8:
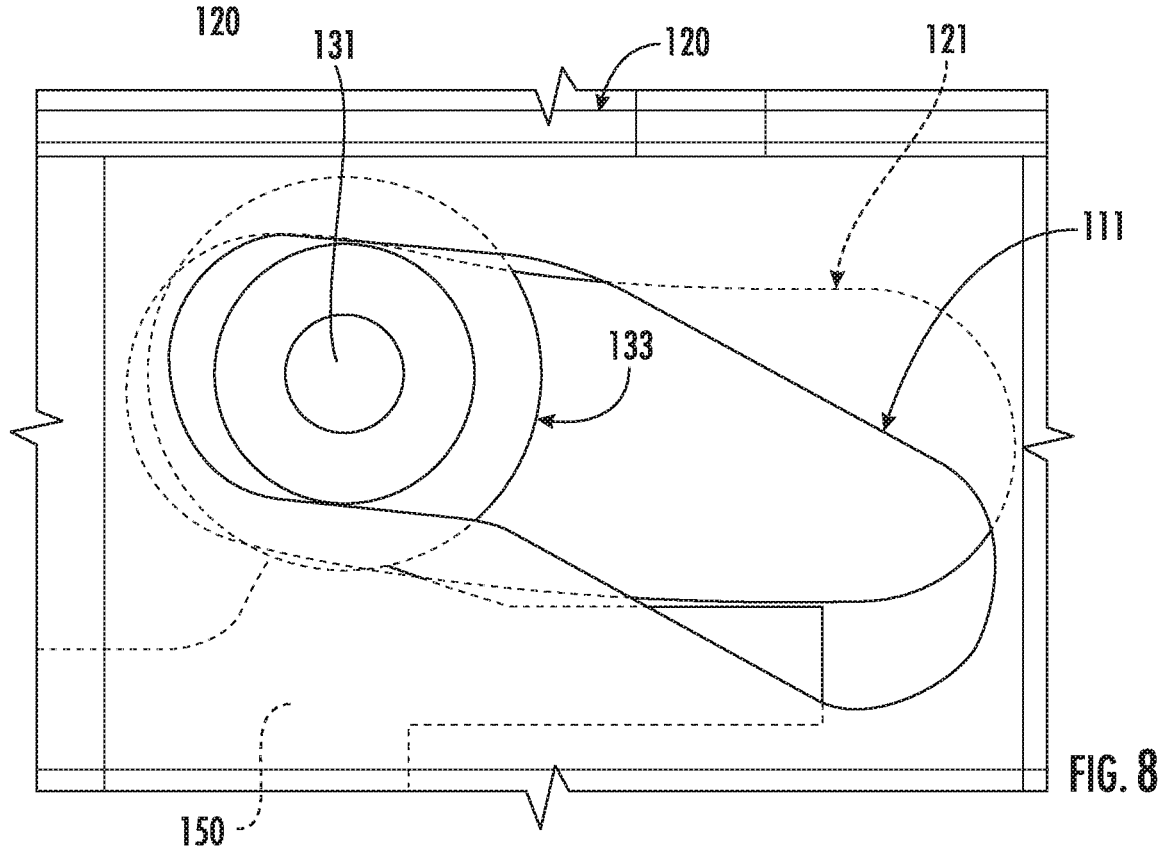
FIG. 8 schematically illustrates the jaw lock of the embodiment shown in FIG. 2.

FIGS. 7 and 8 illustrate actuation of the illustrative surgical instrument of FIG. 2. In FIG. 7, blade 150 has been driven distally from the fully retracted, proximal position shown in FIG. 2 to an intermediate position. As blade 150 travels distally, in the direction indicated by arrow "A", first edges 152a, 152b of blade 150 engage sleeves 133, 134 of pins 131, 132 pushing pins 131, 132 distally along proximal jaw-closing portions 111a, 112a of jaw slots 111 and 112. As pins 131, 132 travel distally along proximal jaw-closing portion 111a, 112a, upper jaw 101 and lower jaw 102 pivot closed. Pins 131, 132 are shown in FIG. 7 at central portions 111b, 112b and upper jaw 101 and lower jaw 102 are in the closed configuration, but not locked.

Figure 10:
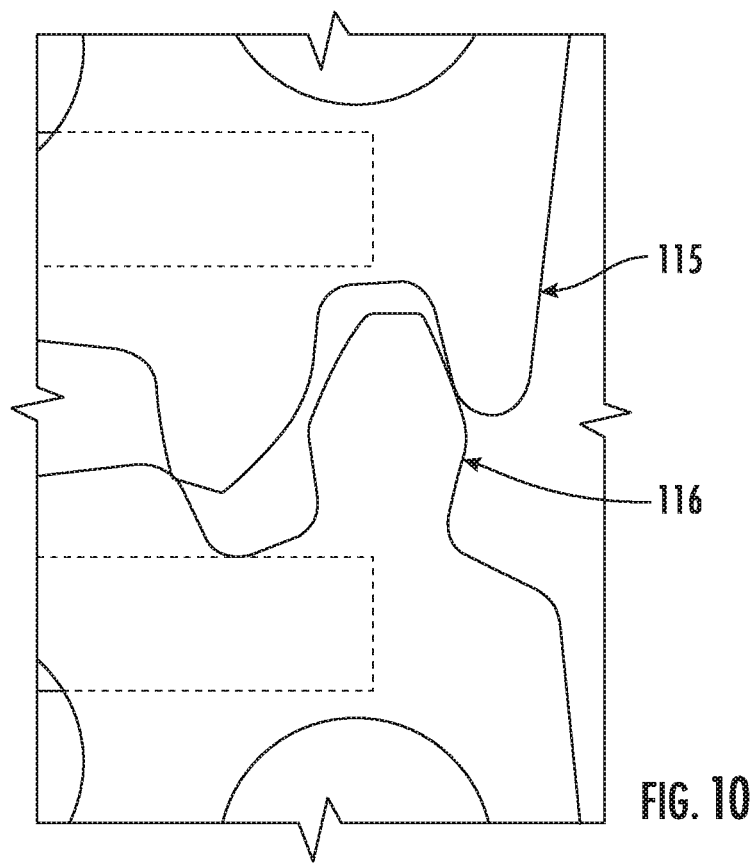
FIG. 10 depicts gear teeth on the distal end portions of the jaws for axial alignment of the jaws in the embodiment of FIG. 2.

As the jaws pivot to a closed configuration, gear teeth 115 and 116, as best seen in FIG. 10 interact to ensure that upper jaw 101 and lower jaw 102 pivot the same amount. If there is asymmetrical movement of upper jaw 101, and lower jaw 102, gear teeth 115 and 116 will force the proper correction to ensure axial alignment is achieved.

In FIG. 8, first edges 152a, 152b of blade 150 have pushed pins 131, 132 to distal end portions 111c, 112c of jaw slots 111, 112. Once at distal end portions 111c, 112c, pins 131, 132 are secured by a friction fit, as they become wedged between jaw slots 111, 112 and upper edges 121d, 122d of clevis slots 121, 122. With pins 131, 132 secured, upper jaw 101 and lower jaw 102 are locked in a closed configuration. At this point, energy may be applied to treat (fuse, cut, etc.) tissue. For example, energy for vessel sealing may generally flow between electrodes on upper jaw 101 and lower jaw 102 and through the tissue of the vessel clamped between the closed jaws. Suitable structures for supplying energy to jaws 101, 102 for treating tissue are within the purview of one skilled in the art. Illustrative structures are disclosed, for example, in U.S. Publication. No. 2015/0250530, the disclosure of which is hereby incorporated by reference in its entirety.

Figure 9:
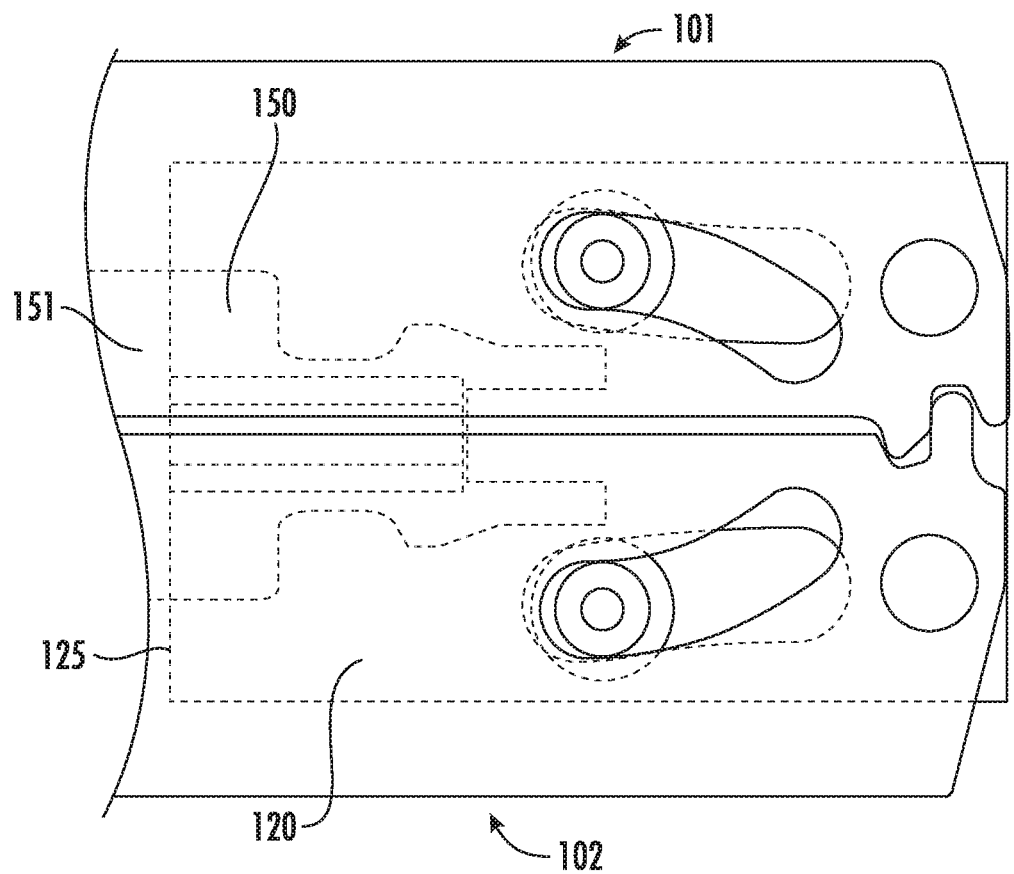
FIG. 9 is a partial cross-sectional side view of the surgical instrument in accordance with the embodiment of FIG. 2 illustrating the jaws in a closed and locked configuration, with the blade advanced distally to cut tissue.

Once secured in distal end portions 111c, 112c, pins 131, 132 have been pushed outwardly and ride above first edges 152a, 152b of blade 150, such that blade 150 may now translate past pins 131, 132. Once tissue has been fused, blade 150 travels distally beyond distal end 125 of clevis 120 to cut tissue as seen in FIG. 9. One of ordinary skill will appreciate that blade 150 may serve multiple functions, including pivoting the jaws closed by pushing the locking pins, enabling the jaw lock, as well as severing tissue.

In use, surgical instruments in accordance with this disclosure may achieve cutting and fusing actions with the actuation of a single input, such as a foot pedal or button. Alternatively, however, the cutting and fusing actions may be separately controlled. Such separate control gives the operator the capability to cut clamped tissue without any tissue fusion taking place (a so-called "cold cut"). If tissue fusion is desired, then a second control is operated, such as a second foot pedal or button. As an alternative to foot pedals or buttons, various other devices may be used to input the cut and fuse commands, such as a switch positioned near a jaw position control input, a voice command, etc. The input device that may be used to control the cutting function may be separate from the device used to control the jaw position and tissue clamping force. Thus, even though a single reciprocating element is used to both actuate jaw position and carry out tissue cutting, two different input devices may be used to control these two functions. These separate inputs prevent an inadvertent over-actuation of the jaw position control input, as may occur when a reciprocating element limit switch has been incorrectly positioned, and unwanted tissue cutting may occur.

In some instances the two (or more) separate inputs are combined in a single type of input device. This single type of input device travels over a first range of motion to command jaw position, and it travels over a second range of motion or moves to a second position outside the first range of motion to control cutting. For example, the reciprocating element's first range of motion, which controls jaw opening and closing, may be controlled by a first range of motion of a spring-loaded pincer mechanism pinched by digits of the hand. The reciprocating element's second range of motion, which is associated with tissue cutting, is then controlled by a second range of motion of the pincer mechanism. This second range of motion is separated from the first range of motion by a clear divider, such as a noticeably higher spring force, a noticeable haptic detent, etc. Elements having two controllable ranges of motion are described, for example, in U.S. Pat. No. 9,314,307, entitled "Grip Force Control for Robotic Surgical Instrument End Effector" which is incorporated herein by reference in its entirety. Similarly, a spring-loaded foot pedal may have two clearly divided ranges of motion, or an input may be difficult to move into a second operating position or direction (akin to a reverse gear "lockout" feature in some automobile manual transmissions), or a second mechanical input must be held in order to move the first input into the second range or position (akin to button that must be pressed on an automobile automatic transmission position selection lever). Thus, while the input is operated to control jaw position, inadvertent tissue cutting is prevented, since the input cannot move into the second range of motion or position without a positive action by the operator each time a transition to the second range of motion or position is desired.

In use, a single tap on one foot pedal may start the cutting function and a single tap on a second pedal may start the fusing function. Control logic prevents the fusing function from beginning if the second pedal is tapped before the reciprocating element is in the correct full distal position. A combination of a tap on one input and a continuous hold on another input may be used. An optional warning (audio, video) may be output that advises the operator that the fusing function has not started. If a tap is used to control the tissue cutting function alone, then the reciprocating element may automatically return to the full or near-proximal position after the cutting, or a second input, such as a second tap or the opening of the jaw position control, may be used to return the reciprocating element to the full- or near-proximal position. Exemplary input devices and input commands for controlling surgical instruments in accordance with this disclosure are further described in U.S. Publication No. US 2017/0189049 A1, the entire disclosures of which is incorporated herein by reference.

Figure 11:
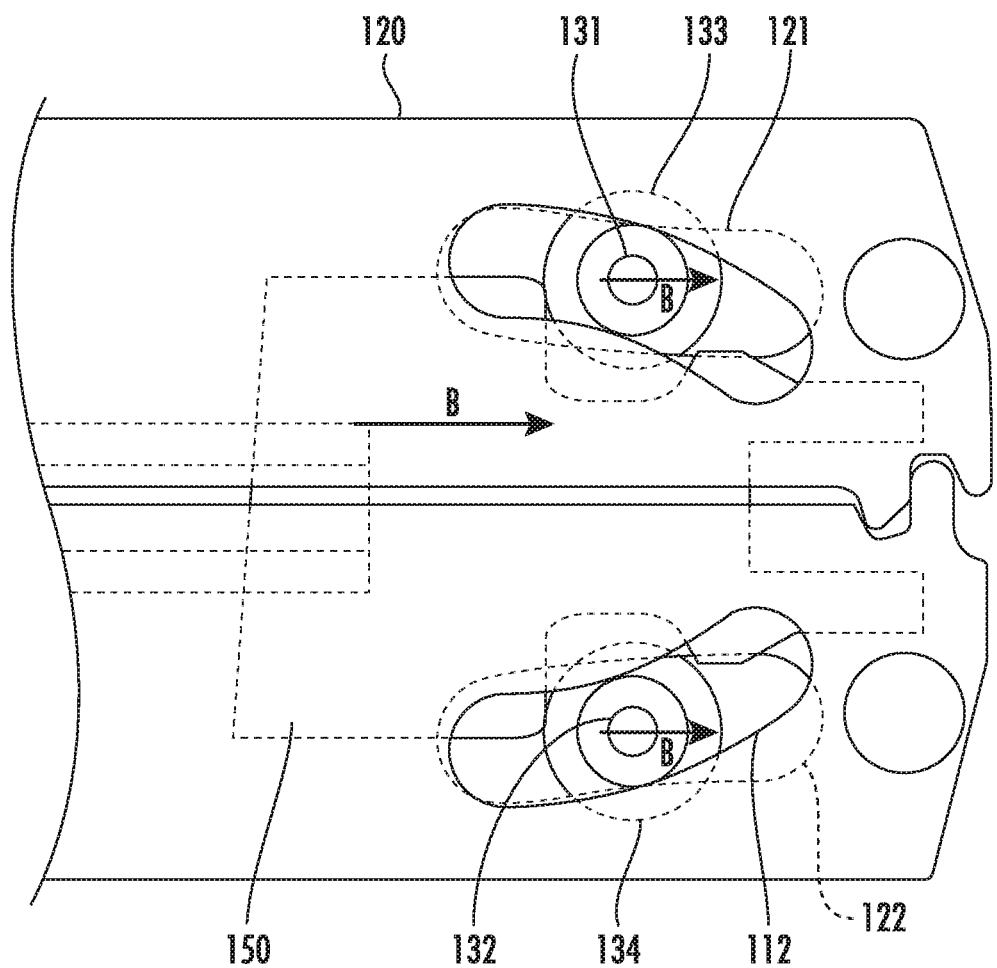
FIG. 11 is a partial cross-sectional view of the surgical instrument in accordance with the embodiment of FIG. 2 showing the blade retracting to unlock the jaws.

FIG. 11 illustrates retraction of blade 150 after tissue has been cut. Upon retraction of blade 150, second edges 154a, 154b of blade 150 engage sleeves 133, 134 of pins 131, 132, forcing pins 131, 132 out of distal end portions 111c, 112c of jaw slots 111, 112. This allows pins 131, 132 to travel back to the proximal home position, as previously shown in FIG. 2. As pins 131, 132 move along proximal portions 111b, 112b to return to the proximal home position, upper jaw 101 and lower jaw 102 pivot back to an open configuration.

Those of ordinary skill in the art reading this disclosure will appreciate that the presently described surgical instruments utilize the blade to pivot jaws from an open position to a closed position, and drive various components distally, rather than relying on I-beams, E-beams, and other similar structures as the drive member as in prior art surgical instruments. Because prior art drive members such as I-beams and other similar structures require a greater instrument width along the length of the instrument to maintain structural integrity, employing the blade as the drive member in accordance with the present disclosure allows for an instrument with a smaller instrument width. Additionally, I-beams typically require horizontally oriented tracks or channels formed within the instrument jaws to accommodate distal travel through the jaws, complicating manufacturing and making it more difficult to achieve electrical isolation of various components. Replacing an I-beam or similar structure with a blade removes the need for any such tracks or channels, thereby simplifying manufacturing and allowing for further reduction of instrument size. Thus, the presently described surgical instruments are ideal for minimally invasive surgery, as their smaller size provides for both ease of manufacturing (resulting in reduced production costs), and reduced patient trauma during minimally invasive surgical procedures.

Figure 12:
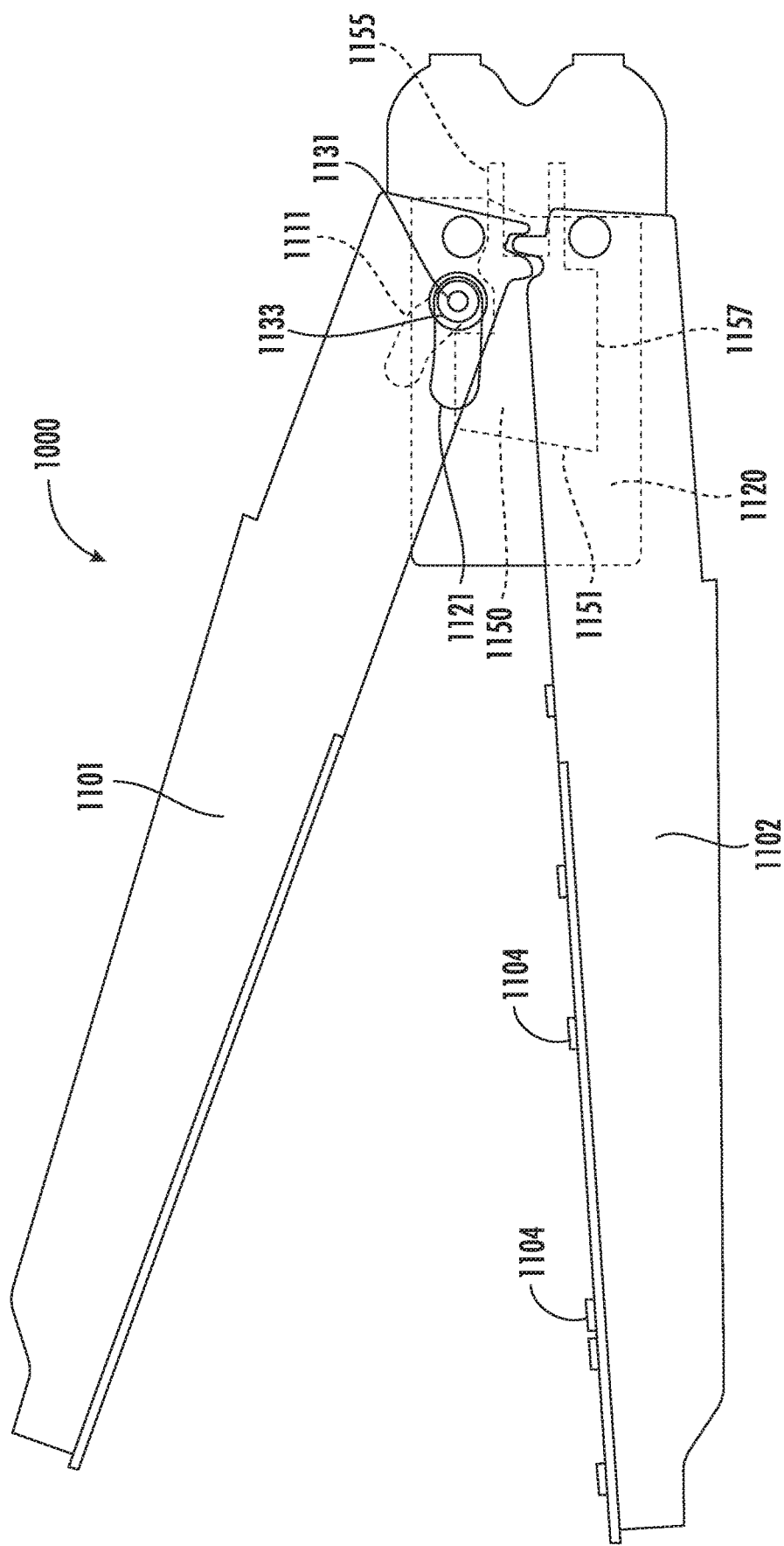
FIG. 12 illustrates an alternate illustrative embodiment of a surgical instrument in accordance with this disclosure having a fixed lower jaw and a pivoting upper jaw.

FIG. 12 illustrates an alternate embodiment including an end effector 1000 having a movable jaw 1101, and a fixed jaw 1102. End effector 1000 may include, blade 1150, pin 1131, sleeve 1133, and jaw slot 1111. As in the previously described embodiment, the jaws 1101, 1102 are mounted to a clevis 1120 having a clevis slot 1121. Movable jaw 1101 of surgical instrument 1000 may function upon movement of blade 1150 to be moved to and locked into the closed position in a substantially similar way to jaw 101 of the embodiment of FIG. 2. As seen in FIG. 12, the fixed nature of jaw 1102 eliminates the need for pins, slots, and notches on blade 1150, as blade 1150 does not have to cause fixed jaw 1102 to pivot. The surgical instrument of FIG. 12 further includes non-conductive stop members 1104. Non-conductive stop members 1104 may be made from any suitable Insulative material such as ceramics, alumina, plastics, or silicone rubber. Non-conductive stop members 1104 prevent sealing surfaces on jaws 1101, 1102 from contacting each other and shorting. In embodiments, the ends of jaws 1101, 1102 may be slightly bowed outwards with respect to the longitudinal axis defined by the shaft, while a substantially central portion of jaws 1101, 1102 are compressed a desired amount in order to achieve desired tissue compression. In embodiments, the distal-most stop members 1104 may be longer than the remaining stop members such that the distal-most stop members contact each other upon jaw closure, ensuring tissue remains within the instrument's cut line and the remainder of the jaws.

Figure 13A:
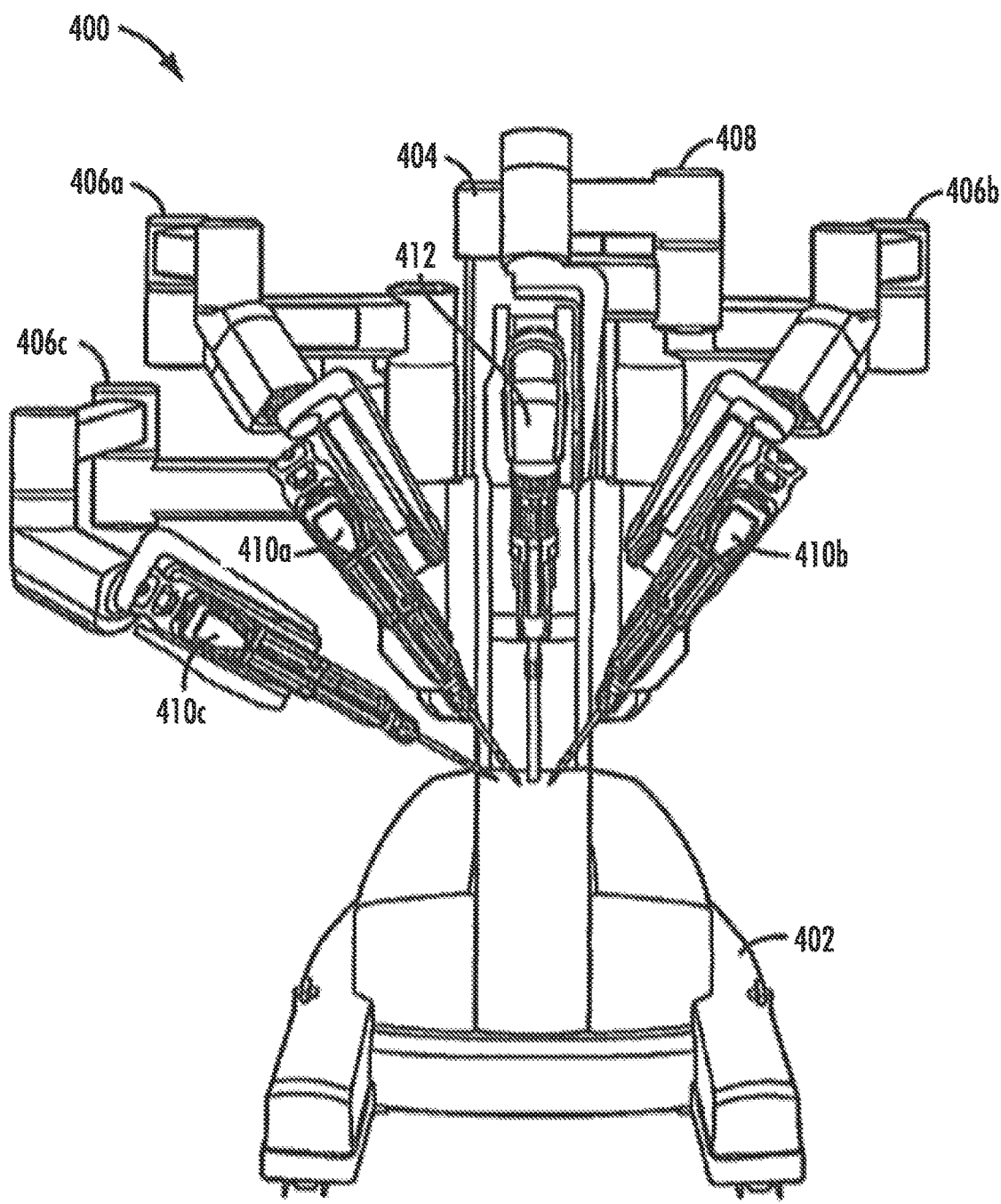
FIG. 13A is a front elevation, diagrammatic view of an exemplary patient side cart of a teleoperated surgical system.

FIG. 13A is a front elevation view of an exemplary embodiment of a patient side cart 400 of a teleoperated surgical system. The patient side cart 400 includes a base 402 that rests on the floor, a support tower 404 mounted on the base 402, and one or more manipulator arms mounted on the support tower 404 and that support surgical instruments and/or vision instruments (e.g., a stereoscopic endoscope). As shown in FIG. 13A, manipulator arms 406a, 406b are arms that support, and transmit forces to manipulate, the surgical instruments used to grasp and move tissue, and arm 408 is a camera arm that supports and moves the endoscope. FIG. 13A also shows a third manipulator arm 406c that is supported on the back side of support tower 404 and that is positionable to either the left or right side of the patient side cart as desired to conduct a surgical procedure.

Interchangeable surgical instruments 410 a, 410 b, 410 c can be installed on the manipulator arms 406a, 406b, 406c, and an endoscope 412 can be installed on the camera arm 108. Those of ordinary skill in the art reading this disclosure will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

Control of the robotic surgical system, including control of the surgical instruments, may be effectuated in a variety of ways, depending on the degree of control desired, the size of the surgical assembly, and other factors. In some embodiments, the control system includes one or more manually operated input devices, such as a joystick, an exoskeletal glove, pincher or grasper assemblies, buttons, pedals, or the like. These input devices control servo motors which, in turn, control the articulation of the surgical assembly. The forces generated by the servo motors are transferred via drivetrain mechanisms, which transmit the forces from the servo motors generated outside the patient's body through an intermediate portion of the elongate surgical instrument 410 to a portion of the surgical instrument inside the patient's body distal from the servo motor.

Figure 13B:
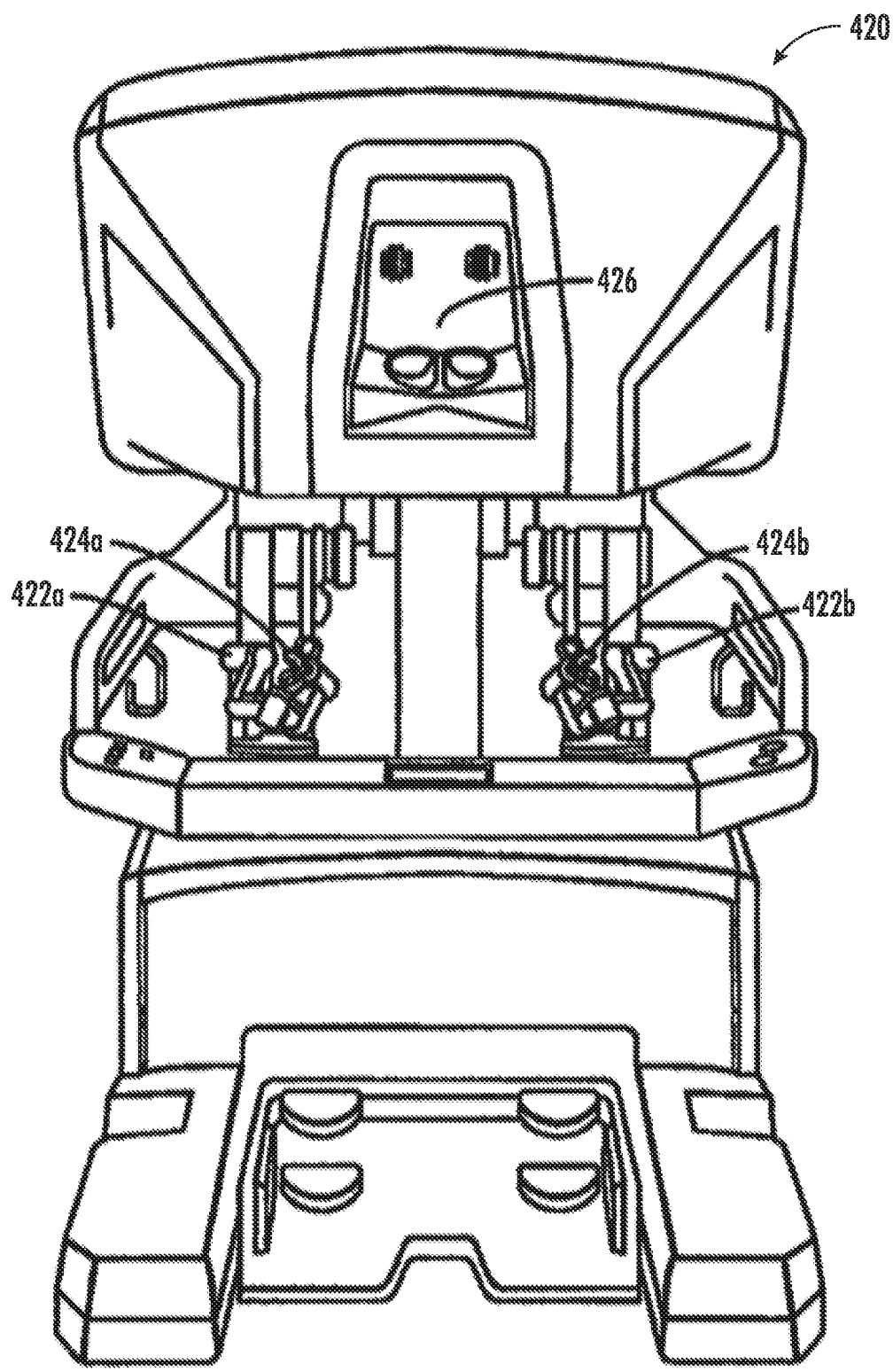
FIG. 13B is a front elevation, diagrammatic view of an exemplary surgeon's console of a teleoperated surgical system.

FIG. 13B is a front elevation view of an exemplary surgeon's console 420 of a teleoperated surgical system for controlling the insertion and articulation of surgical instruments 410. The surgeon or other system operator manipulates input devices by moving and repositioning input devices within console 420. As illustrated in the exemplary embodiment of FIG. 13B, the surgeon's console is equipped with master controllers or master input devices. As illustrated in FIG. 13B, master input devices may include left and right multiple degree-of-freedom (DOF) master tool manipulators (MTM's) 422a, 422b, which are kinematic chains that are used to control the surgical tools (which include the endoscope and various cannulas mounted on arms 406, 408 of the patient side cart 400). Each MTM may include an area for surgeon or operator input. For example, as shown in FIG. 13B, each MTM 422a, 422b may include a pincher assembly 424a, 424b. The surgeon grasps a pincher assembly 424a, 424b on each MTM 422a, 422b, typically with the thumb and forefinger, and can move the pincher assembly to various positions and orientations. When a tool control mode is selected, each MTM 422 is coupled to control a corresponding manipulator arm 406 for the patient side cart 400, as those of ordinary skill in the art are familiar. The pincher assembly is typically used to operate a surgical end effector (e.g., scissors, grasping retractor, needle driver, hook, forceps, spatula, etc.) at the distal end of an instrument 410.

Surgeon's console 420 also can include an image display system 426. In an exemplary embodiment, the image display is a stereoscopic display wherein left side and right side images captured by the stereoscopic endoscope 412 are output on corresponding left and right displays, which the surgeon perceives as a three-dimensional image on display system 426.

The surgeon's console 420 is typically located in the same operating room as the patient side cart 400, although it is positioned so that the surgeon operating the console may be outside the sterile field. One or more assistants may assist the surgeon by working within the sterile surgical field (e.g., to change tools on the patient side cart, to perform manual retraction, etc.). Accordingly, the surgeon may operate remote from the sterile field, and so the console may be located in a separate room or building from the operating room. In some implementations, two consoles 420 (either co-located or remote from one another) may be networked together so that two surgeons can simultaneously view and control tools at the surgical site.

For additional details on the construction and operation of general aspects of a teleoperated surgical system such as described herein, see, e.g., U.S. Pat. Nos. 6,493,608 and 6,671,581, the entire disclosure of each of which is incorporated herein by reference.

Figure 13C:
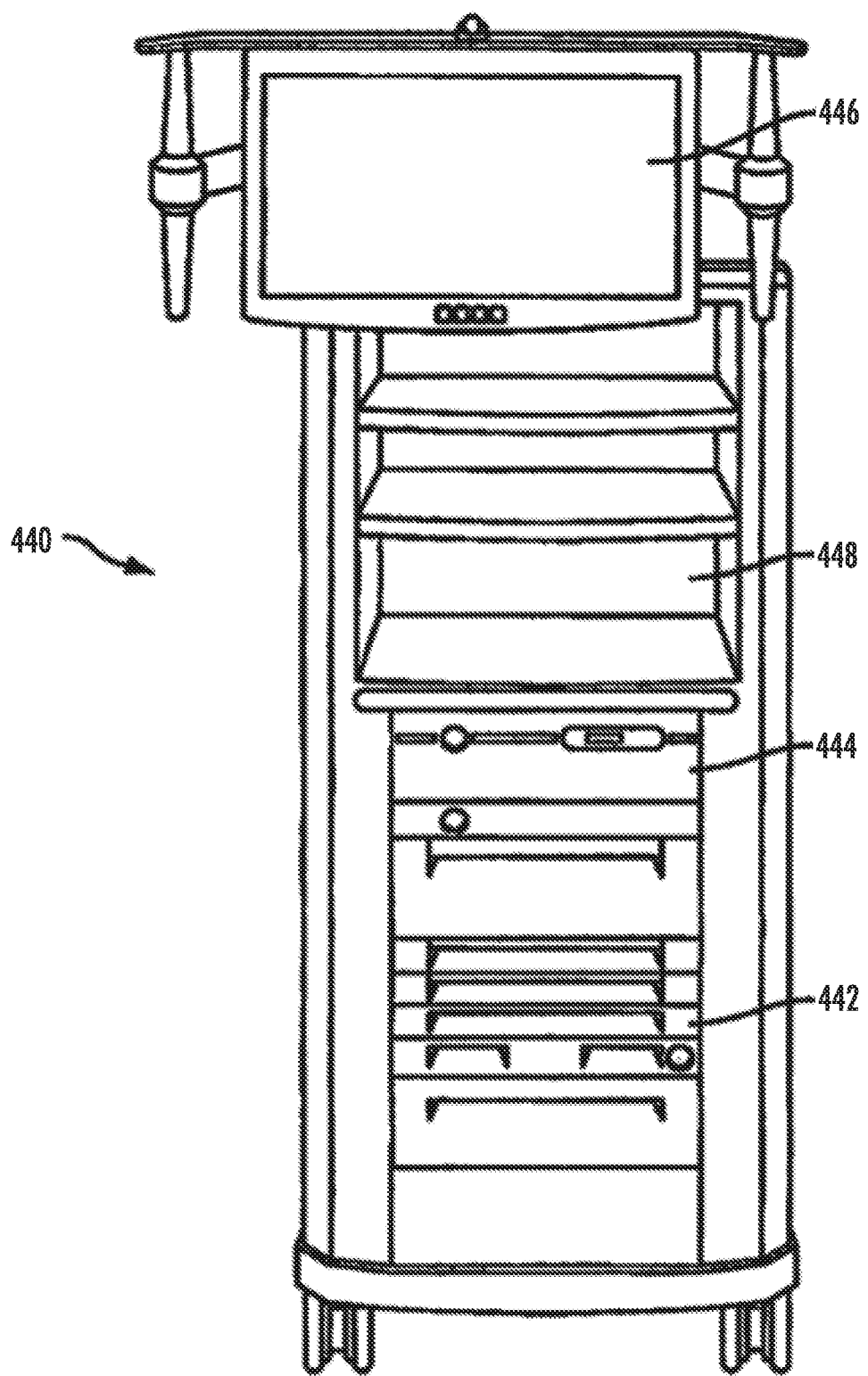
FIG. 13C is a front elevation, diagrammatic view of an exemplary auxiliary control/vision cart of a teleoperated surgical system.

As shown in FIG. 13C, the auxiliary control/vision cart 440 includes an optional display 446 (e.g., a touchscreen monitor), which may be mounted elsewhere, such as on the patient side cart 400. The auxiliary control/vision cart 440 further includes space 448 for optional auxiliary surgical equipment, such as electrosurgical units, insufflators, and/or other flux supply and control units. The patient side cart 400 (FIG. 13A) and the surgeon's console 420 (FIG. 13B) are coupled via optical fiber communications links to the auxiliary control/vision cart 440 so that the three components together act as a single teleoperated minimally invasive surgical system that provides an intuitive telepresence for the surgeon.

With reference to FIG. 14, an exemplary embodiment of a teleoperated surgical instrument 500 that may support a previously described end effector of the present disclosure is depicted. As shown in FIG. 14, the instrument 500 generally includes a proximal housing 510 at its proximal end; proximal housing 510 may include an instrument memory or storage device (not shown). The memory can perform a number of functions when the instrument is loaded on a manipulator arm (not shown). For example, the memory can provide a signal verifying that the instrument is compatible with that particular surgical system. Additionally, the memory may identify the instrument and end effector type (whether it is a scalpel, a needle grasper, jaws, scissors, a clip applier, an electrocautery blade, or the like) to the surgical system so that the system can reconfigure its programming to take full advantage of the instrument's specialized capabilities. As further discussed below, the memory may include specifics on the architecture of the instrument, and include particular values that should be employed in control algorithms, such as tool compliance and gain values.

Proximal housing 510 also may include a force/torque drive transmission mechanism (not shown) for receiving output from motors of the manipulator arm 406, the force/torque drive transmission mechanism transmitting the output from the motors to an end effector 530 of the instrument through an instrument shaft 520 mounted to the transmission mechanism. Exemplary surgical robotic instruments, instrument/manipulator arm interface structures, and data transfer between the instruments and servomechanism is more fully described in U.S. Pat. No. 6,331,181, the full disclosure of which is incorporated herein by reference.

The end effector 530 is disposed at the distal end of the shaft 520 and may be connected thereto by a clevis (not shown) that supports and mounts the end effector 530 relative to the instrument shaft 520. As embodied herein, the shaft 520 may be a relatively flexible structure that can bend and curve. Alternatively, the shaft 520 may be a relatively rigid structure that does not permit traversing through curved structures. Optionally, in some embodiments, the instrument 500 also can include a multi-degree of freedom (DOF) articulable wrist structure that supports the end effector 530 and permits multi-DOF movement of the end effector in arbitrary pitch and yaw. Those having ordinary skill in the art are familiar with a variety of wrist structures used to permit multi-DOF movement of a surgical instrument end effector.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument comprising:
   an elongated shaft defining a longitudinal axis; and
   an end effector mounted on a distal end portion of the elongated shaft, the end effector including:
   a first jaw and a second jaw, the first and second jaws moveable between an open position to receive tissue between the jaws and a closed position to grasp tissue between the jaws;
   the first jaw including a jaw slot having a jaw closing portion and a jaw locking portion;
   a pin positioned within the jaw slot;
   a blade including a cutting edge and a notch, the notch defining a first edge configured to engage and distally advance the pin relative to the end effector through the jaw closing portion of the jaw slot to pivot the jaws to the closed position and, upon further distal movement of the blade, distally advance the pin relative to the end effector through the jaw locking portion of the jaw slot, wherein the pin engages the jaw locking portion of the jaw slot in a friction fit to secure the pin into a locked position relative to the jaw slot; and wherein the first edge of the notch of the blade is configured to translate distal to the pin once the pin engages the jaw locking portion of the jaw slot.

2. The surgical instrument of claim 1, wherein the notch of the blade defines a second edge configured to engage the pin upon retraction of the blade, urging the pin back to through the jaw closing portion to a jaw opening portion of the jaw slot, wherein the second edge extends further laterally outward from the longitudinal axis of the shaft than the first edge.

3. The surgical instrument of claim 1, wherein the jaw slot has a width that is substantially the same as a width of the pin.

4. The surgical instrument of claim 1, further comprising gear teeth at a proximal portion of the first jaw.

5. The surgical instrument of claim 1, wherein the blade further includes a drive engagement portion.

6. The surgical instrument of claim 5, wherein the drive engagement portion is substantially U-shaped.

7. The surgical instrument of claim 1, wherein the second jaw is stationary.

8. The surgical instrument of claim 1, wherein the second jaw is moveable, the second jaw further including a jaw slot having a proximal jaw closing portion and a distal jaw locking portion.

9. The surgical instrument of claim 1 further comprising a wrist assembly including a clevis.

10. The surgical instrument of claim 9, wherein the clevis includes a clevis slot, the pin extending into the clevis slot.

11. The surgical instrument of claim 9 wherein the clevis slot includes a proximal portion and a distal portion.

12. The surgical instrument of claim 2 wherein the jaw opening portion of the jaw slot is oriented at an angle of about 5 to about 30 degrees with respect to the jaw closing portion of the jaw slot.

13. The surgical instrument of claim 11, wherein the distal portion of the clevis slot is oriented at an angle of about 5 to about 30 degrees from with respect to the longitudinal axis defined by the shaft.

* * * * *